United States Patent
Nagai et al.

(10) Patent No.: US 12,105,050 B2
(45) Date of Patent: Oct. 1, 2024

(54) DAMAGE EVALUATION DEVICE AND DAMAGE EVALUATION METHOD

(71) Applicant: IHI CORPORATION, Tokyo (JP)

(72) Inventors: Yuuki Nagai, Tokyo (JP); Masahiro Hato, Tokyo (JP); Hiroaki Hatanaka, Tokyo (JP)

(73) Assignee: IHI CORPORATION, Tokyo (JP)

( * ) Notice: Subject to any disclaimer, the term of this patent is extended or adjusted under 35 U.S.C. 154(b) by 302 days.

(21) Appl. No.: 17/879,919

(22) Filed: Aug. 3, 2022

(65) Prior Publication Data

US 2022/0381741 A1 Dec. 1, 2022

Related U.S. Application Data (63) Continuation of application No. PCT/JP2021/008757, filed on Mar. 5, 2021.

(30) Foreign Application Priority Data

Jun. 12, 2020 (JP) ................. 2020-102049

(51) Int. Cl.
- *G01N 29/04* (2006.01)
- *G01N 29/06* (2006.01)
- *G01N 29/26* (2006.01)
- *G01N 33/207* (2019.01)

(52) U.S. Cl.
CPC ......... *G01N 29/043* (2013.01); *G01N 29/069* (2013.01); *G01N 29/26* (2013.01); *G01N 33/207* (2019.01); *G01N 2291/267* (2013.01)

(58) Field of Classification Search
CPC ...... G10N 29/00; G10N 29/04; G10N 29/046; G10N 29/06; G10N 29/069; G10N 29/26; G01N 33/00; G01N 33/20; G01N 33/207; G01N 2291/267
See application file for complete search history.

(56) References Cited

U.S. PATENT DOCUMENTS

| | | |
|---|---|---|
| 8,976,017 B1 | 3/2015 | Cannon |
| 2017/0131220 A1 | 5/2017 | Buelsing et al. |
| 2021/0190731 A1 | 6/2021 | Ueda et al. |

FOREIGN PATENT DOCUMENTS

| | | |
|---|---|---|
| CN | 107121501 A | 9/2017 |
| JP | 2003-207489 A | 7/2003 |
| JP | 2005-156305 A | 6/2005 |
| JP | 2008-249441 A | 10/2008 |

(Continued)

OTHER PUBLICATIONS

Machine translation of JP-2009198249-A (Year: 2009).*

(Continued)

*Primary Examiner* — Nguyen Q. Ha (57) ABSTRACT

A damage evaluation device includes: a phased array probe that irradiates an ultrasonic signal from a surface of an inspection metal toward an inside of the inspection metal and detects a reflection signal reflected in a predetermined region inside the inspection metal; and an arithmetic processor. The arithmetic processor sets planes parallel to each other in an inspection region, calculates pixel data by quantifying the reflection signal from segments set in each of the planes; calculates a scattering degree of the pixel data, and evaluates damage of the inspection metal based on the scattering degree.

10 Claims, 8 Drawing Sheets

(56) References Cited

FOREIGN PATENT DOCUMENTS

| | | | |
|---|---|---|---|
| JP | 2009198249 A | * | 9/2009 |
| JP | 2012-053060 A | | 3/2012 |
| JP | 2013-019715 A | | 1/2013 |
| JP | 2017-151107 A | | 8/2017 |
| JP | 2019-045217 A | | 3/2019 |
| JP | 2019-138700 A | | 8/2019 |
| WO | 2019/044554 A1 | | 3/2019 |
| WO | 2019/117120 A1 | | 6/2019 |

OTHER PUBLICATIONS

Japan Patent Office, "Decision to Grant a Patent," issued in Japanese Patent Application No. 2020-102049, which is a Japanese counterpart of U.S. Appl. No. 17/879,919, mailed on Dec. 20, 2023, 1 page.
Australian Government IP Australia, "Examination report No. 1 for standard patent application", issued in Australian Patent Application No. 2021289697, which is a counterpart to U.S. Appl. No. 17/879,919, on Jul. 14, 2023, 5 pages.

* cited by examiner

DAMAGE EVALUATION DEVICE AND DAMAGE EVALUATION METHOD

CROSS REFERENCE TO RELATED APPLICATIONS

This application is a continuation application of International Application No. PCT/JP2021/008757, now WO 2021/250955 A1, filed on Mar. 5, 2021, which claims priority to Japanese Patent Application No. 2020-102049, filed on Jun. 12, 2020, the entire contents of which are incorporated by reference herein.

BACKGROUND

1. Technical Field

The present disclosure relates to a damage evaluation device and a damage evaluation method.

2. Description of the Related Art

In the field of strength of materials, a phenomenon in which deformation of an object proceeds due to stress at high temperature is referred to as "creep". Inside an object with creep occurring therein, a crack inducing voids may be generated. In this regard, JP 2019-45217 A (PTL 1) proposes a method for evaluating damage inside a metallic material which is at an early stage of a process growing into a crack, using a phased array ultrasonic flaw detection device. The phased array ultrasonic flaw detection device scans ultrasonic waves irradiated toward the inside of the welded portion of a test piece, receives the reflected waves of ultrasonic waves, and evaluates the damage of the welded portion by acquiring the intensity distribution of the reflected waves.

SUMMARY

In the technique disclosed in PTL 1, the evaluation value may vary depending on the sensitivity of the device during the measurement or the contact state of the ultrasonic probe. In this case, the evaluation with high accuracy becomes difficult.

The present disclosure is made to solve conventional problems as described above. The object of the present disclosure is to provide a damage evaluation device and a damage evaluation method capable of evaluating damage inside a metal with high accuracy.

A damage evaluation device according to the present disclosure includes: a phased array probe configured to irradiate an ultrasonic signal from a surface of an inspection metal, which is a metal to be evaluated, toward an inside of the inspection metal and detect a reflection signal reflected in a predetermined region inside the inspection metal; and an arithmetic processor configured to: set planes parallel to each other in the predetermined region, calculate pixel data by quantifying the reflection signal from segments set in each of the planes; calculate a scattering degree of the pixel data, and evaluate damage of the inspection metal based on the scattering degree.

A damage evaluation method according to the present disclosure includes: irradiating an ultrasonic signal from a surface of an inspection metal, which is a metal to be evaluated, toward an inside of the inspection metal by a phased array probe; detecting a reflection signal reflected in a predetermined region in the inspection metal; calculating pixel data by setting planes parallel to each other in the predetermined region and quantifying the reflection signal from segments set in each of the planes; calculating a scattering degree of the pixel data; and evaluating the damage of the inspection metal based on the scattering degree.

The quantification in the calculation of the pixel data may be executed for a reflection signal of the maximum intensity extracted from the reflection signal from the segments arranged in a direction orthogonal to the planes.

According to the present disclosure, it is possible to evaluate damage inside a metal with high accuracy.

DESCRIPTION OF THE EMBODIMENTS

Figure 1:
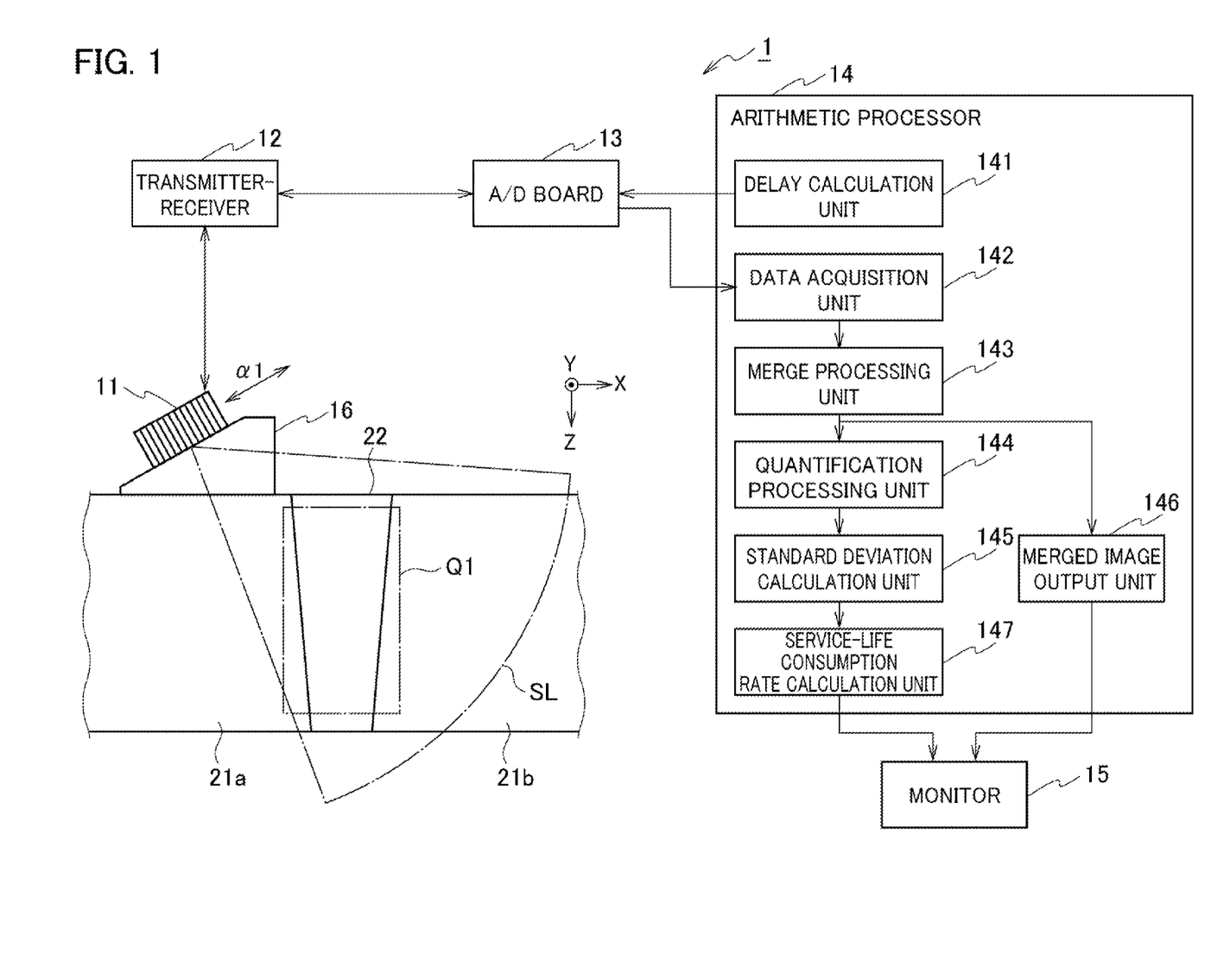
FIG. 1 is a block diagram showing a configuration of a damage evaluation device according to an embodiment.

Some exemplary embodiments are described below with reference to the drawings. FIG. 1 is a block diagram showing a configuration of a damage evaluation device according to the present embodiment. An example shown in FIG. 1 detects damage such as a crack or defect occurring in a welded portion of a member connecting two metals by welding and diagnoses a service-life consumption rate of the welded portion. In the present disclosure, the "service-life consumption rate" represents a ratio of a consumption period to a service-life which is a period until a metal is fractured due to aging.

Configuration of First Embodiment

As shown in FIG. 1, a damage evaluation device 1 according to the present embodiment detects damage in a welded portion 22 as an example of an object to be evaluated. It is assumed that this damage is caused, for example, in the welded portion 22 when the ends of two metal plates 21a and 21b are butted against each other and welded. In the device shown in FIG. 1, a left-right direction is defined as an X direction, a direction orthogonal to the sheet is defined as a Y direction, and an up-down direction is defined as a Z direction. The X, Y and Z directions are orthogonal to each other. The X and Y directions are, for example, parallel to the metal plates 21a and 21b. The Z direction is, for example, the thickness direction of each of the metal plates 21a and 21b. A plane including the X direction and the Z direction (i.e., the X-Z plane) includes a traveling direction and a scanning direction of an ultrasonic beam, which will be described later.

The damage evaluation device 1 includes a base 16, a phased array probe 11, a transmitter-receiver 12, an A/D board 13, an arithmetic processor 14, and a monitor 15.

The base 16 is provided on a surface of a metal plate (the metal plate 21a in the present embodiment) including an evaluation object. The base 16 has an inclined surface in contact with the phased array probe 11. The base 16 is made of acrylic or the like. Glycerin is applied between the base 16 and the metal plate 21a to remove an air layer.

The evaluation object in the present embodiment is the welded portion 22 joining the metal plates 21a and 21b. The welded portion 22 may form an overfill of a welding bead. Therefore, the base 16 is provided with the inclined surface as described above. With this, the ultrasonic beam can be incident on the welded portion 22 at a position far from the welding bead in the X direction, and interference of the overfilled bead with the base 16 can be avoided. However, the present disclosure is not limited to this, and the surface of the base 16 to which the phased array probe 11 contacts may be a surface parallel to the metal plate 21a.

The phased array probe 11 has multiple (e.g., 64) ultrasonic transducers arranged in a one-dimensional direction. The ultrasonic transducers are successively provided (i.e., arrayed) in a direction al shown in FIG. 1. Here, the direction al is an extending direction of the inclined surface, which is in contact with the phased array probe 11, on the X-Z plane. By controlling an oscillation timing (i.e., a delay time of oscillation) for each of ultrasonic transducers, the ultrasonic beam is irradiated toward a region SL in the X-Z plane shown in FIG. 1. Furthermore, the phased array probe 11 is scanned in a direction orthogonal to the X-Z plane (i.e., the Y direction), thereby moving the irradiation region of the ultrasonic beam in the Y direction. That is, the phased array probe 11 irradiates the metal to be evaluated with the ultrasonic beam (ultrasonic signal) from the surface of the metal toward the inside of the metal, and receives a reflection signal (reflected ultrasonic wave) reflected in a predetermined region inside the metal. Hereinafter, a metal as an evaluation object (inspection object) is referred to as "inspection metal" for convenience of explanation.

Figure 2:
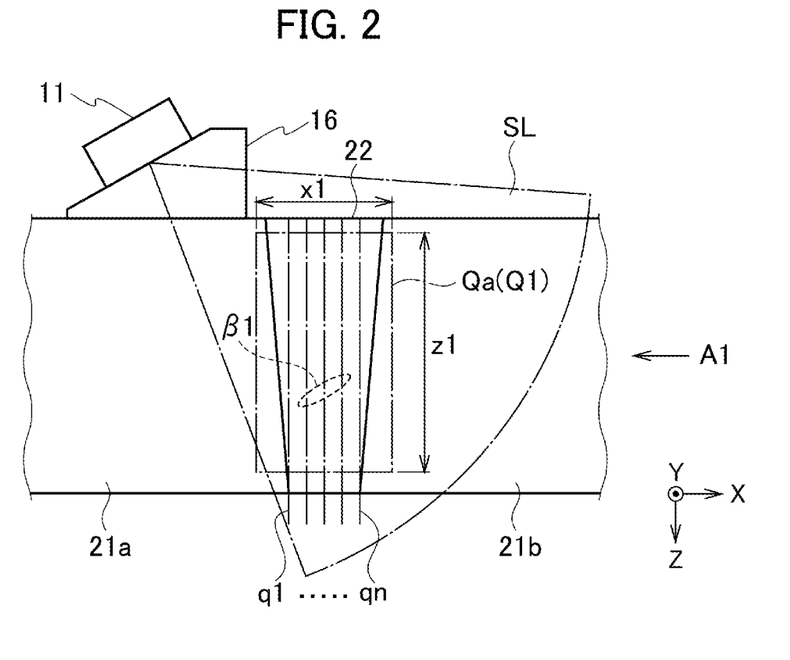
FIG. 2 is an explanatory view showing an inspection region of an X-Z plane of a metal to be inspected by the damage evaluation device according to the embodiment.
Figure 3:
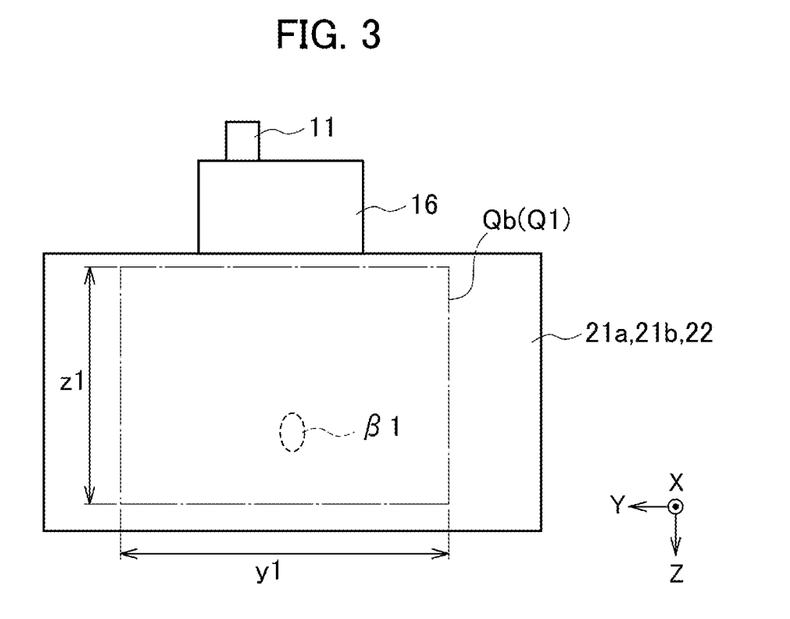
FIG. 3 is an explanatory view showing an inspection region of a Y-Z plane of the metal to be inspected by the damage evaluation device according to the embodiment.

A detection region by the phased array probe 11 will be described with reference to FIGS. 2 and 3. FIG. 2 is a view showing the metal plates 21a and 21b viewed from the Y direction. FIG. 3 is a view showing the metal plates 21a and 21b from a direction A1 indicated by the arrow in FIG. 2. The direction A1 is a direction opposite to the X direction.

By the irradiation of the ultrasonic beam from the phased array probe 11, the reflection signal from the region Qa including the welded portion 22 shown in FIG. 2 is obtained. As a result, the reflection signal in a region defined by the lines x1 and z1 shown in FIG. 2 is obtained.

The irradiation of the ultrasonic beam and the obtainment of the reflection signal are performed while scanning the phased array probe 11 in the Y direction. As a result, the reflection signal from the region Qb defined by the lines y1 and z1 shown in FIG. 3 is obtained. That is, a three-dimensional region (hereinafter referred to as "inspection region Q1") of a cuboid defined by the lines x1, y1, and z1 is set as a detection region (a predetermined region inside a metal) by the ultrasonic beam.

As shown in FIG. 1, the transmitter-receiver 12 outputs electrical signals for driving the ultrasonic transducers provided in the phased array probe 11. In addition, the transmitter-receiver 12 receives the reflection signal detected by each ultrasonic transducer.

The A/D board 13 converts digital drive signals for the ultrasonic transducers, which are outputted from a delay calculation unit 141 as described later, to analog signals. The A/D board 13 digitizes the reflection signal of the ultrasonic wave detected by the transmitter-receiver 12 and outputs the digitized signal to a data acquisition unit 142 as described later.

The arithmetic processor 14 includes a delay calculation unit 141, a data acquisition unit 142, a merge processing unit 143, a quantification (digitization) processing unit 144, a standard deviation calculation unit 145, a merged image output unit 146, and a service-life consumption rate calculation unit 147. The arithmetic processor 14 can be configured as an integrated computer including, for example, a central processing unit (CPU) and a storage device such as RAM, ROM, hard disk, etc.

The delay calculation unit 141 controls the oscillation timing (delay time) of the ultrasonic transducers provided in the phased array probe 11, and outputs a control signal for changing the irradiation area of the ultrasonic beam.

The data acquisition unit 142 acquires (obtains) a reflection signal, which is detected by each ultrasonic transducer of the phased array probe 11 and then digitized by the A/D board 13.

The merge processing unit 143 generates a merged image based on the intensity of each reflection signal (hereinafter referred to as "reflection signal intensity") detected in the three-dimensional inspection region Q1 shown in FIGS. 2 and 3. A detailed description will be given below.

As described above, by irradiating the ultrasonic beam using the phased array probe 11 and scanning the phased array probe 11 in the Y direction, the reflection signal from the inspection region Q1 set in the welded portion 22 is obtained.

As shown in FIG. 2, planes q1 to qn are set in the inspection region Q1. These planes are parallel to the plane Y-Z. The number n is 64, for example. Minute regions (pixels) (hereinafter referred to as "segments") are set in each plane q1 to qn.

Figure 4:
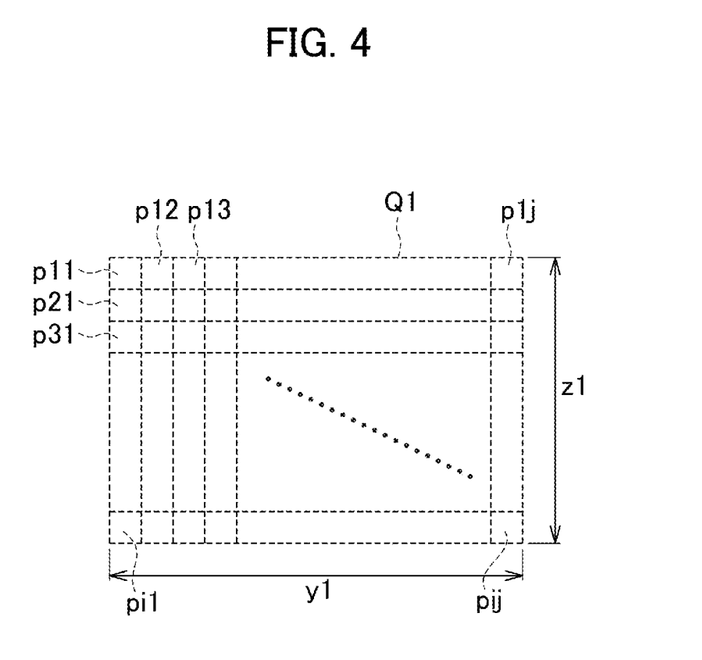
FIG. 4 is an explanatory view showing a merged image obtained by projecting in the X direction a segment having the maximum reflection signal intensity among segments of planes, wherein the segments are arranged in the X direction and the planes are parallel to the Y-Z plane.

When the reflection signal of the ultrasonic beam is obtained for each segment of each of the planes q1 to qn, the merge processing unit 143 compares intensities (hereinafter referred to as "reflection signal intensities") of the reflection signals of the segments of each of the planes q1 to qn along the X direction. The merge processing unit 143 extracts the maximum value from the reflection signal intensities in the X direction. Further, the merge processing unit 143 generates a merged image indicating the maximum value for each pixel. For example, as shown in FIG. 4, the merged image in which a rectangular plane having the vertical line z1 and the horizontal line y1 is divided into (i×j) pixels $p_{11}$ to $p_{ij}$ is obtained. The pixel $p_{11}$ is set to have the maximum value among the reflection signal intensities of the segments (minute regions) corresponding to the pixel $p_{11}$ when the planes q1 to qn are projected in the X direction.

Therefore, for example, as shown in FIGS. 2 and 3, when a damaged portion β1 such as a crack or defect exists in the inspection region Q1, the reflection signal intensity of the pixel, which corresponds to the damaged portion β1 among the pixels $p_{11}$ to $p_{ij}$ shown in FIG. 4, increases.

As shown in FIG. 1, the merged image output unit 146 outputs (displays) the merged image generated by the merge processing unit 143 to the monitor 15.

The quantification processing unit 144 converts the reflection signal intensity of each of the pixels $p_{11}$ to $p_{ij}$ in the merged image to a numerical value corresponding to the intensity. For example, the quantification processing unit 144 sets a numerical value (hereinafter referred to as "pixel data") for each of the pixels $p_{11}$ to $p_{ij}$ in accordance with the intensity of the reflection signal. Here, the numerical value has a value in the range of 1 to 100, for example. Accordingly, each of the pixels $p_{11}$ to $p_{ij}$ shown in FIG. 4 is set to have pixel data corresponding to the respective intensity of the reflection signal. That is, the quantification processing unit 144 has a function of calculating pixel data, which is data obtained by quantifying (digitizing) the reflection signal intensity of each pixel.

The standard deviation calculation unit 145 calculates the standard deviation of the pixel data set in the pixels $p_{11}$ to $p_{ij}$ shown in FIG. 4. As is well known, the standard deviation can be calculated by the following equation (1).

$$\sigma^2 = \frac{1}{n}\sum_{k=1}^{n}(x_k - \mu)^2 \quad (1)$$

In the equation (1), k is the pixel number specified by (i, j), n is the number of pixels (i.e., "i×j"), μ is the average value of the pixel data, σ is the standard deviation, and $x_k$ is the pixel data in each pixel.

The standard deviation calculation unit 145 has a function as a scattering degree calculation unit which calculates a degree of scattering of pixel data in the merged image. In the present embodiment, the standard deviation is given as an example indicating the scattering degree of the pixel data. However, the present disclosure is not limited to this, and the scattering degree of the numerical values may be calculated by other methods.

The service-life consumption rate calculation unit (evaluation unit) 147 evaluates the damage of the inspection metal based on the standard deviation calculated by the standard deviation calculation unit 145 and a preset calibration curve. The service-life consumption rate calculation unit 147 includes a storage unit (not shown) such as a memory. The storage unit stores a calibration curve f1 (see FIG. 8) in advance. The calibration curve f1 indicates the relationship between the usage time (service time) of the test metal and the standard deviation. The usage time for defining the calibration curve f1 includes a fracture prediction time Te. The fracture prediction time Te is a predicted maximum value of the usage time, that is, the time when the fracture of the inspection metal is predicted.

The calibration curve f1 can be obtained by performing creep tests of samples or past statistical data. Hereinafter, a method of creating the calibration curve f1 will be described with reference to the graphs shown in FIGS. 6A, 6B and 6C.

Figure 6A:
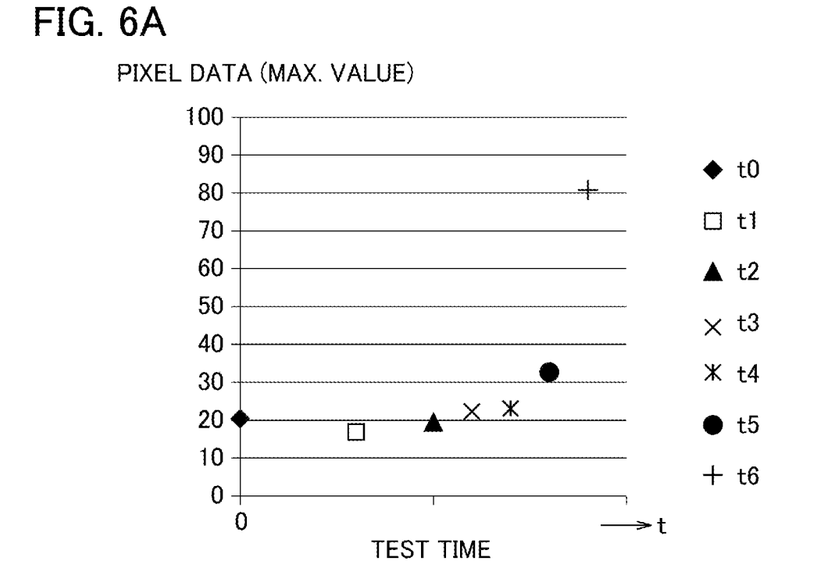
FIG. 6A is a graph showing a relationship between the maximum value of each pixel data in the merged image and the test time.
Figure 6B:
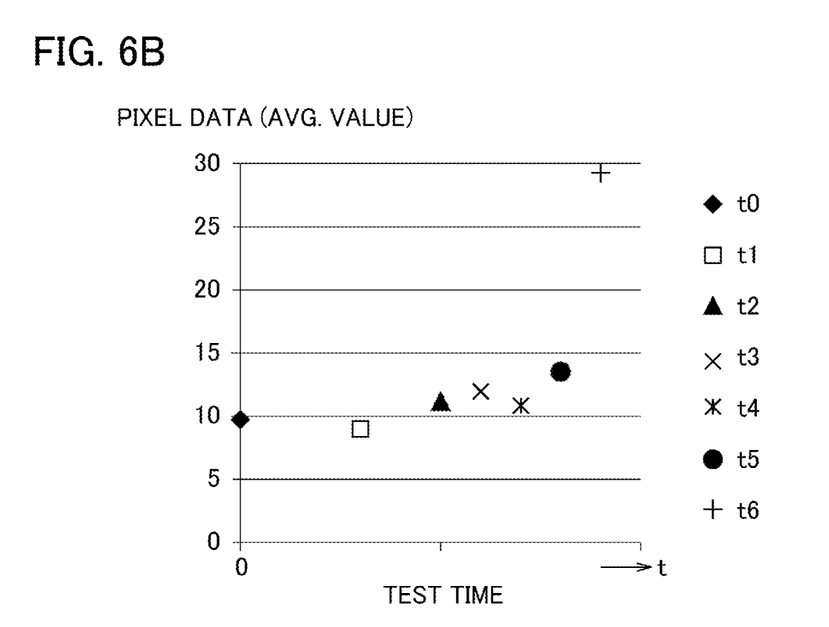
FIG. 6B is a graph showing a relationship between the average value of each pixel data in the merged image and the test time.
Figure 6C:
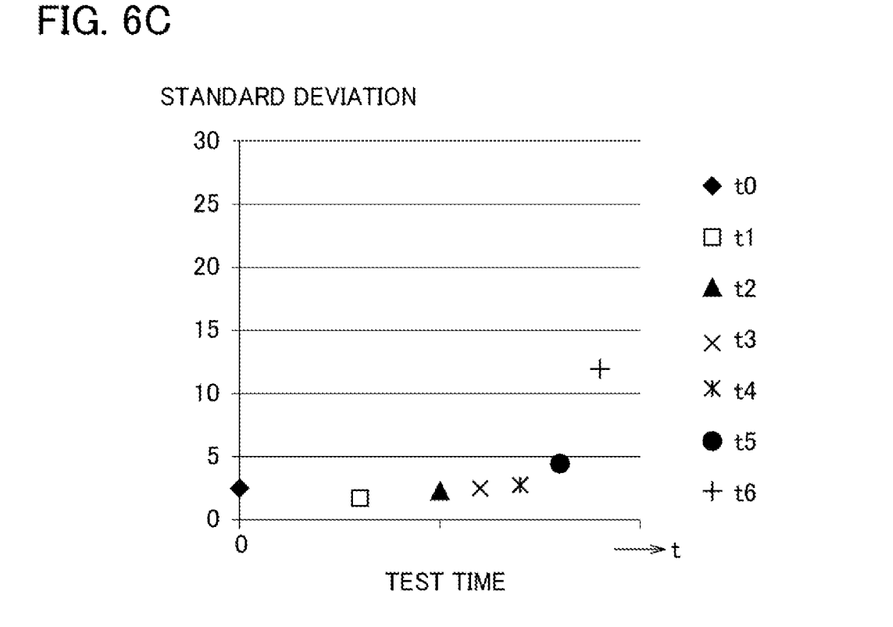
FIG. 6C is a graph showing a relationship between the standard deviation of each pixel data in the merged image and the test time.

A sample of the test metal is prepared, and a state where the sample is placed under an operating environment is maintained for a long time. During a period until the sample is damaged or fractured, the change in pixel data ($p_{11}$ to $p_{ij}$ in FIG. 4) relative to the test time (elapsed time) is measured. Further, the maximum value, average value and standard deviation of each pixel data are calculated. FIG. 6A shows the change of the maximum value to the elapse of the test time. FIG. 6B shows the change of the mean value to the elapse of the test time. FIG. 6C shows the change of the standard deviation to the elapse of the test time.

From the graphs of FIGS. 6A to 6C, it is understood that the maximum value, mean value and standard deviation tend to increase with increasing the test time. The calibration curve f1 shown in FIG. 8 is obtained by repeating such a test multiple times.

Figure 8:
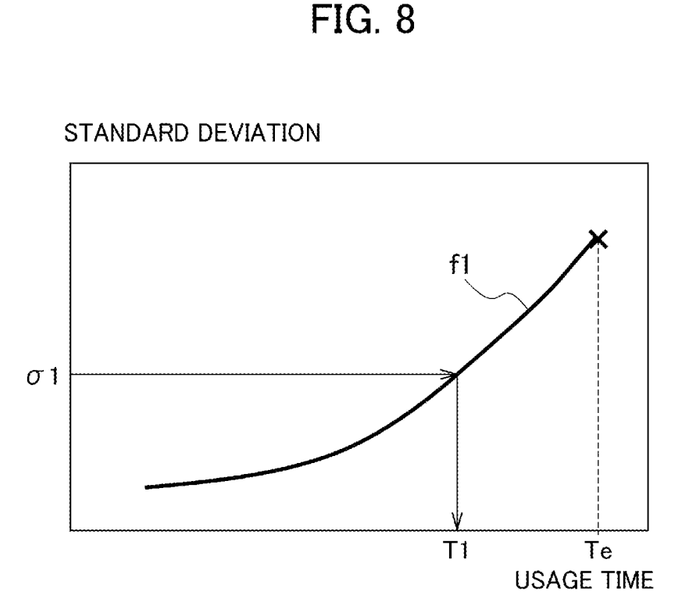
FIG. 8 is a graph of a calibration curve showing a relationship between the standard deviation and the usage time.

The service-life consumption rate calculation unit 147 obtains the current usage time T1 by applying the standard deviation σ calculated from the actually measured pixel data of the inspection metal (e.g., pixel data of pixels $p_{11}$ to $p_{ij}$ shown in FIG. 4) to the graph f1 shown in FIG. 8. Further, the service-life consumption rate is calculated based on the fracture prediction time Te and the usage time T1. For example, the service-life consumption rate can be calculated by (T1/Te).

As shown in FIG. 1, the monitor 15 displays the merged image output from the merged image output unit 146. The monitor 15 displays the service-life consumption rate calculated by the service-life consumption rate calculation unit 147 and informs the user of the service-life consumption rate of the inspection metal.

Operation of First Embodiment

Next, processes of the damage evaluation device 1 according to the present embodiment will be described with reference to the flowchart shown in FIG. 5.

Figure 5:
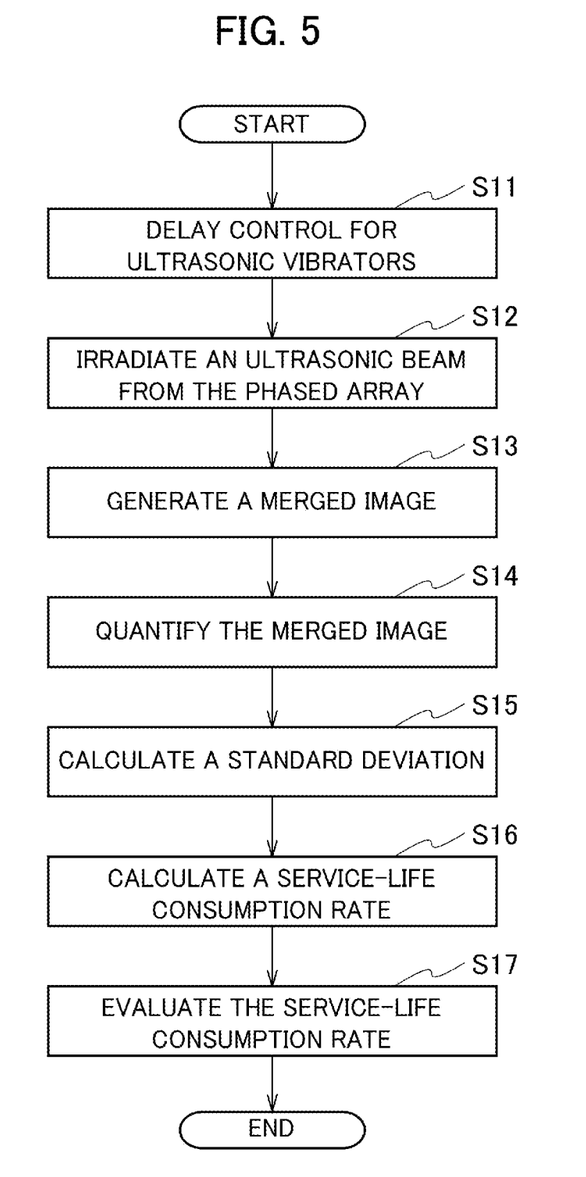
FIG. 5 is a flowchart showing processes by the damage evaluation device according to the first embodiment.

First, in step S11 shown in FIG. 5, the arithmetic processor 14 outputs delay control signals to the ultrasonic transducers provided in the phased array probe 11.

In step S12, the arithmetic processor 14 drives the phased array probe 11 to irradiate the inspection metal with the ultrasonic beam while performing delay control. As a result, the ultrasonic beam can be irradiated to the inspection region Q1 defined by the lines x1, y1, and z1 shown in FIGS. 2 and 3.

In step S13, the arithmetic processor 14 generates a merged image. Specifically, for the planes q1 to qn shown in FIG. 2, the arithmetic processor 14 generates an image as the merged image by projecting a segment having the maximum reflection signal intensity in the X direction among the segments of the planes q1 to qn arranged in the X direction. In other words, a reflection signal having the maximum intensity, which is extracted from the reflection signal intensities of the segments of the planes q1 to qn arranged in the X direction, is quantified as pixel data, and a merged image by the pixel data is generated. As a result, as shown in FIG. 4, the merged image with the pixels $p_{11}$ to $p_{ij}$ each having the maximum value of the reflection signal intensity in the X direction is generated.

In step S14, the arithmetic processor 14 quantifies the merged image. Specifically, the arithmetic processor 14 sets pixel data, which corresponds to the intensity of the reflection signal of the ultrasonic beam, to the pixels $p_{11}$ to $p_{ij}$ shown in FIG. 4.

In step S15, the arithmetic processor 14 calculates the standard deviation of the pixel data. Specifically, the arithmetic processor 14 calculates the standard deviation σ by substituting the number of pixels (i×j) for "n" in the above equation (1), and substituting the average value of the pixel data for "μ".

In step S16, the arithmetic processor 14 calculates the service-life consumption rate of the inspection metal based on the standard deviation σ and the calibration curve f1 shown in FIG. 8.

In step S17, the arithmetic processor 14 evaluates a degree of damage of the inspection metal (i.e., the welded portion 22 in the present embodiment) based on the calculated service-life consumption rate. In the present embodiment, the standard deviation σ is calculated from the pixel data of the pixels $p_{11}$ to $p_{ij}$, and the degree of damage of the metal is evaluated by considering the standard deviation σ and the calibration curve f1. Therefore, a highly accurate evaluation can be performed in comparison with the conventional method.

Effect of First Embodiment

The damage evaluation device of the present embodiment provides the following operations and effects.
(1) An inspection metal is irradiated with an ultrasonic beam to obtain its reflection signal reflected inside the metal. An inspection region Q1 (a predetermined region) defined by sides x1, y1, and z1 shown in FIGS. 2 and 3 inside the metal is set, and planes q1 to qn parallel to the Y-Z plane are set in the inspection region Q1. The data of the reflected wave detected for each segment of each of the planes q1 to qn is projected in the X direction to extract the maximum value, and a merged image is generated. Further, pixels $p_{11}$ to $p_{ij}$ of the merged image are quantified (digitized), and the standard deviation of the quantified (digitized) pixel data is calculated. The test metal is evaluated based on the calculated standard deviation and the calibration curve f1 shown in FIG. 8. Therefore, it is possible to highly accurately evaluate damage such as a crack or defect occurring in the inspection metal such as the welded portion 22.
(2) The standard deviation is used as the scattering degree of the pixel data. Therefore, the damage of the metal can be evaluated by a simple calculation, and the load on the device for calculation can be reduced.
(3) The calibration curve f1 (see FIG. 8) showing the relationship between the usage time and the standard deviation is created based on the statistical data obtained in the past, and the damage of the metal is evaluated using this calibration curve. Therefore, the damage of the metal can be evaluated with higher accuracy.

In the present embodiment, the standard deviation is used as an example of index representing the scattering degree. However, the present disclosure is not limited to this and other methods can be used. In the present embodiment, as shown in FIG. 2, the multiple planes q1 to qn parallel to the Y-Z plane is set in the inspection region Q1. However, the present disclosure is not limited to this, and the multiple planes q1 to qn parallel to each other can be set in any direction.

That is, there may be provided a configuration in which multiple planes parallel to each other are set in the inspection region Q1 (predetermined region), the reflection signal is obtained for each segment set in each plane, and a merged image, which is an image extracting the maximum value from among the reflection signal intensities of pixels in a direction orthogonal to the planes, is generated.

Modified Example of First Embodiment

Next, a modified example of the first embodiment will be described. In the modified example, when calculating the standard deviation, the maximum value of each pixel data is normalized and then the standard deviation is calculated.

Figure 7A:
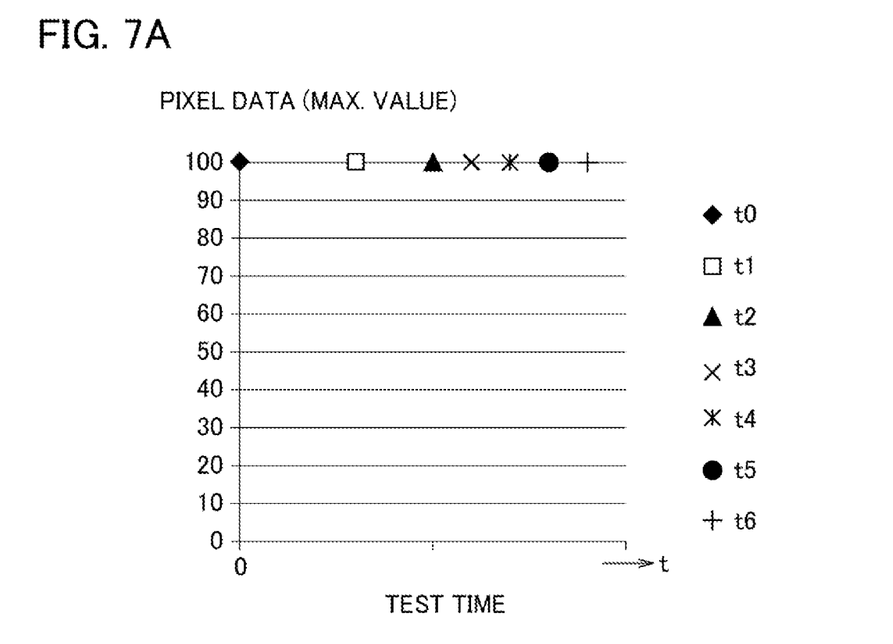
FIG. 7A is a graph showing a relationship between the maximum value and the test time when the maximum value of each pixel data of the merged image is normalized.
Figure 7B:
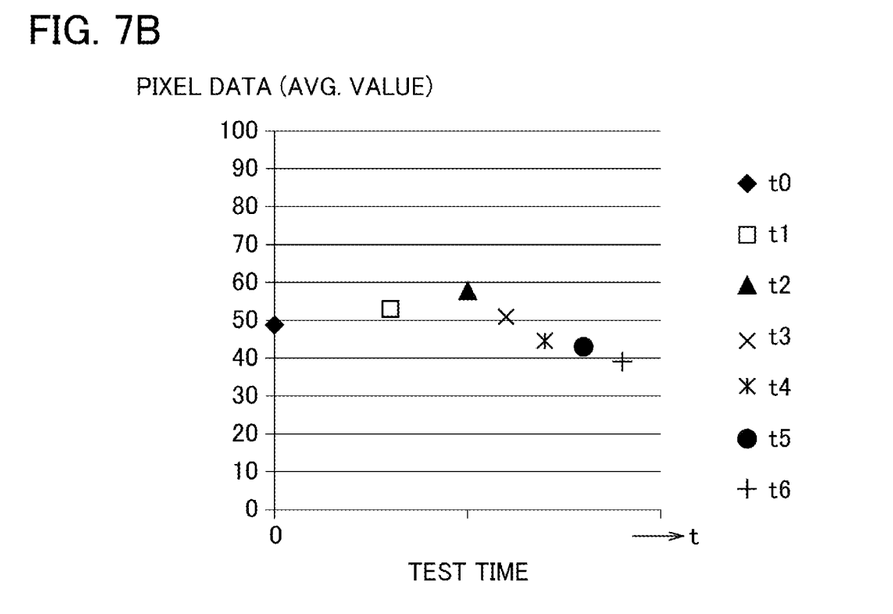
FIG. 7B is a graph showing a relationship between the average value of each pixel data and the test time when the maximum value of each pixel data of the merged image is normalized.
Figure 7C:
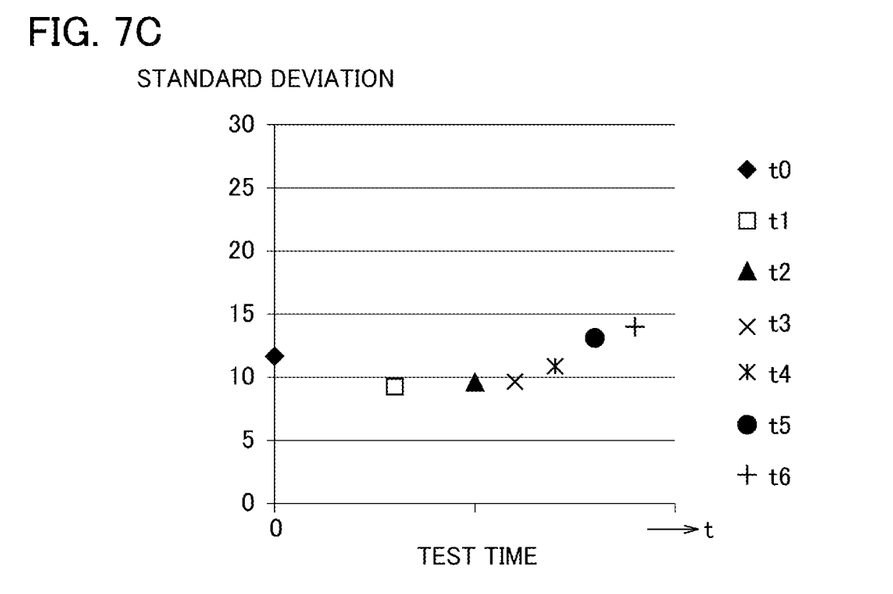
FIG. 7C is a graph showing a relationship between the standard deviation of each pixel data and the test time when the maximum value of each pixel data of the merged image is normalized.

Specifically, as shown in FIG. 7A, when creating a calibration curve based on data obtained by past statistical data or creep tests, each pixel data is normalized such that the maximum values of the pixel data for every test time has the same value. Then, as shown in FIG. 7B, an average value is calculated based on the pixel data in which the maximum value is normalized. A standard deviation is calculated based on the pixel data in which the maximum value is normalized as shown in FIG. 7C. Then, a calibration curve f1 (see FIG. 8) is created based on the calculated standard deviation.

When evaluating the inspection metal, the standard deviation is calculated after normalizing the maximum value of the pixel data of each pixel $p_{11}$ to $p_{ij}$ acquired by the inspection. Based on the calculated standard deviation and the aforementioned characteristic curve, damage such as a crack or defect in the test metal is evaluated.

By normalizing the maximum value of the pixel data, even when the maximum value of the pixel data in each pixel $p_{11}$ to $p_{ij}$ varies, the influence of this variation can be reduced and the inspection metal can be evaluated with higher accuracy. In the modified example, the maximum value of the pixel data is normalized. However, a similar technical effect can be obtained by normalizing the average value of the pixel data before calculating the standard deviation.

DESCRIPTION OF SECOND EMBODIMENT

Next, a second embodiment will be described. In the second embodiment, similarly to the first embodiment described above, multiple planes q1 to qn parallel to the Y-Z plane are set in the three-dimensional inspection region Q1 (predetermined region) defined by lines x1, y1, and z1 shown in FIGS. 2 and 3.

Further, in the second embodiment, the intensity of the reflection signal is quantified for each segment of each of the planes q1 to qn and the pixel data is acquired. That is, pixels $p_{11}$ to $p_{ij}$ shown in FIG. 4 are set for each of the planes q1 to qn, and pixel data for each of the planes q1 to qn is calculated. That is, (i×j) pieces of pixel data shown in FIG. 4 are calculated for each of the planes q1 to qn, and ((i×j)×n) pieces of pixel data are acquired.

The standard deviation is calculated for the pixel data in the same manner as in the first embodiment, and the damage of the inspection metal is evaluated based on the calculated standard deviation. According to this configuration, since the damage of the metal is evaluated based on more pixel data existing in the inspection region Q1, it is possible to evaluate the damage of the metal more accurately, compared with the first embodiment.

Although embodiments of the present invention have been described above, it should not be understood that the statements and drawings forming part of this disclosure are intended to limit the present invention. Various alternative embodiments, further embodiments, and operational techniques will be apparent to those skilled in the art from this disclosure.

What is claimed is:

1. A damage evaluation device comprising:
a phased array probe configured to irradiate an ultrasonic signal from a surface of an inspection metal, which is a metal to be evaluated, toward an inside of the inspection metal and detect a reflection signal reflected in a predetermined region inside the inspection metal; and
an arithmetic processor configured to:
set planes parallel to each other in the predetermined region;
calculate pixel data by quantifying the reflection signal from segments set in each of the planes;
calculate a scattering degree of the pixel data; and
evaluate damage of the inspection metal based on the scattering degree.

2. The damage evaluation device according to claim 1, wherein
the quantification in the calculation of the pixel data is executed for a reflection signal of the maximum intensity extracted from the reflection signal from the segments arranged in a direction orthogonal to the planes.

3. The damage evaluation device according to claim 2, wherein
the scattering degree is a standard deviation.

4. The damage evaluation device according to claim 1, wherein
the scattering degree is a standard deviation.

5. The damage evaluation device according to claim 3, wherein
the arithmetic processor normalizes either the maximum value or the average value of the pixel data to calculate the standard deviation.

6. The damage evaluation device according to claim 4, wherein
the arithmetic processor normalizes either the maximum value or the average value of the pixel data to calculate the standard deviation.

7. The damage evaluation device according to claim 1, wherein
the arithmetic processor evaluates the damage of the inspection metal based on a standard deviation and a calibration curve stored in advance in the arithmetic processor, and
the calibration curve is a curve indicating a relationship between the standard deviation and usage time of the test metal until time when the test metal is fractured.

8. The damage evaluation device according to claim 7, wherein:
the arithmetic processor displays a service-life consumption rate of the inspection metal on a monitor as an evaluation of the damage of the inspection metal, and
the service-life consumption rate is a ratio of the usage time of the inspection metal to the time of fracture of the inspection metal predicted based on the calibration curve.

9. A damage evaluation method including:
irradiating an ultrasonic signal from a surface of an inspection metal, which is a metal to be evaluated, toward an inside of the inspection metal by a phased array probe;
detecting a reflection signal reflected in a predetermined region in the inspection metal;
calculating pixel data by setting planes parallel to each other in the predetermined region and quantifying the reflection signal from segments set in each of the planes;
calculating a scattering degree of the pixel data; and
evaluating the damage of the inspection metal based on the scattering degree.

10. The damage evaluation method according to claim 9, wherein
the quantification in the calculation of the pixel data is executed for a reflection signal of the maximum intensity extracted from the reflection signal from the segments arranged in a direction orthogonal to the planes.

* * * * *